United States Patent [19]
Gongora et al.

[11] Patent Number: 4,876,389
[45] Date of Patent: Oct. 24, 1989

[54] PROCESS FOR THE PRODUCTION OF ORGANIC POLYSULPHIDES AND CATALYST SYSTEM FOR ITS USE

[75] Inventors: Henri Gongora, Billere; Yves Darche, Orthez, both of France

[73] Assignee: Societe Nationale Elf Aquitaine (Production), Courbevoie, France

[21] Appl. No.: 126,008

[22] Filed: Nov. 27, 1987

[30] Foreign Application Priority Data

Nov. 28, 1986 [FR] France .................. 86 16615

[51] Int. Cl.$^4$ .................. C07C 148/00
[52] U.S. Cl. .................. 568/26; 568/45
[58] Field of Search .................. 568/26, 45

[56] References Cited

U.S. PATENT DOCUMENTS

| | | | |
|---|---|---|---|
| 2,237,625 | 4/1941 | Olin | 562/594 |
| 2,720,543 | 10/1955 | Crouch et al. | 568/45 |
| 3,022,351 | 2/1962 | Mihm et al. | 568/26 |
| 3,038,013 | 6/1962 | Warner | 568/21 |
| 4,575,569 | 3/1986 | Edwards | 568/45 |

FOREIGN PATENT DOCUMENTS

| | | |
|---|---|---|
| 0025944 | 3/1971 | European Pat. Off. . |
| 1553249 | 12/1968 | France . |

Primary Examiner—Mary E. Ceperley
Attorney, Agent, or Firm—Stevens, Davis, Miller & Mosher

[57] ABSTRACT

Process for the production of organic polysulphides of the type R—$S_n$—R, where R is a hydrocarbon group and n a number from 2 to 8, by heating one or more mercaptans with sulphur, in the presence of a catalyst; the catalyst consists of the combination of a mercaptan with an alkene oxide and an alkaline base.

19 Claims, No Drawings

PROCESS FOR THE PRODUCTION OF ORGANIC POLYSULPHIDES AND CATALYST SYSTEM FOR ITS USE

The invention relates to the manufacture of organic polysulphides by the action of sulphur on a mercaptan, in liquid medium, in the presence of a novel catalyst system.

Organic polysulphides are products which have diverse industrial applications, particularly in cutting oils, as extreme pressure additives. Their preparation in liquid medium, by reaction between elemental sulphur and a mercaptan, is known. It generally requires the presence of a catalyst, such as amine, alkanolamine, inorganic base, mercaptide or alcoholate. Such processes have been described, for example, in French Pat. No. 1,381,265 and in U.S. Pat. No. 3,275,693, 3,314,999 and 3,340,324. It is found, however, that these different catalysts have certain disadvantages: either the yield leaves something to be desired or the purity of the product is not satisfactory or, yet again, the polysulphide obtained gives off a disturbing odour. Thus, amines produce an odour and a certain turbidity, while mercaptides and alcoholates require the use of a solvent, which causes turbidity in the manufactured product and increases the costs of manufacture.

By virtue of the use of a novel, special catalyst, the present invention avoids the abovementioned disadvantages and permits regular, continuous production, without solvent, in very good yields, of polysulphides of good purity, without disturbing odour, without turbidity or undesirable colour and with a very low content of residual —SH. It applies to many polysulphides of the $R—S_n—R$ type, where R is a hydrocarbon, especially aliphatic, alicyclic or aryl, group, it being possible for the mean value of n to vary between 2 and 8 and especially 3 and 5. Since the polysulphides most widely employed at present are those in which the groups R are linear or branched alkyls, the process of the invention enables these to be easily obtained. It is thus possible to produce polysulphides with $C_1$-$C_{20}$ and, in particular, $C_6$-$C_{18}$, alkyl groups as R, which include the highly useful compounds containing tertiary alkyl groups, particularly $C_8$-$C_{16}$, more especially tert-nonyl and tertdodecyl polysulphides, in which n is from 3 to 5.

The process according to the invention, which consists in heating with sulphur one or more mercaptans in the liquid state, in the presence of a catalyst, is characterized in that the catalyst consists of the combination of a mercaptan with an alkene oxide and an alkaline base. $C_2$-$C_4$ alkenes are particularly suitable.

The combination which is used as catalyst according to the invention may be denoted by the expression

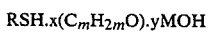

RSH.x($C_mH_{2m}O$).yMOH where R denotes a hydrocarbon, in particular alkyl, group, like those referred to above; x is the number of moles of alkene oxide per mole of mercaptan RSH, and y that of the moles of alkaline base, with M denoting an alkali metal, especially Na or K. Ethylene oxide, being more economical, is preferably emloyed as the alkene oxide, but it may, if desired, be replaced or mixed with another alkene oxide.

In general, x has a value from 1 to 20 and, in most cases, from 4 to 12; it depends on the surfactant nature required for the synthesis of the polysulphide, on the compatibility of the catalyst with the polysulphide to be produced and on the homogeneity of the catalyst system.

As for y, this is preferably approximately from 0.01 to 1 or, better, from 0.1 to 0.5.

The catalyst system described above is employed as such, in order to be added to the bulk of mercaptan which is to be converted into polysulphide, or else diluted with a portion of this mercaptan. Although the proportion of catalyst in relation to the mercaptan to be converted may vary quite widely, it is preferably approximately 0.1 to 5% by weight.

One way of preparing the novel catalyst system consists in first mixing 1 mole of a mercaptan RSH with $\alpha y$ moles ($\alpha = 1$ to 1.5) of alkaline base MOH, this mixture being preferably homogenized hot; it is possible, in particular, to operate for several hours between 50° and 100° C., in particular for 4 to 6 hours between 75° and 85° C. Alkene oxide is then injected into the liquid obtained in this manner, so as to fix the desired proportion x, indicated earlier, of $C_mH_{2m}O$ groups.

This injection is preferably carried out at a pressure of 0.2 to 4 bars at a temperature of the order of 80° to 120° C., depending on the nature of the mercaptan which is treated; the fixation of the alkene oxide generally takes 1 to 10 hours.

It is recommendable, after these operations, to degas the decompressed reaction mixture, in order to remove the dissolved excess oxide; the degassing is advantageously performed with the aid of an inert gas such as nitrogen.

It is good practice to filter the liquid obtained before it is used for the production of the polysulphide.

A plant for the preparation of the catalyst system essentially comprises a reactor in which the fixation of the alkene oxide onto the alkali-treated mercaptan takes place, as well as a vessel for degassing excess oxide, supporting suitable columns. These units and their accessories may advantageously form an integral part of a plant for producing polysulphide from a mercaptan, so as to provide it with the necessary catalyst.

As a general rule, the process according to the invention, employing the novel catalyst, may be conducted like the known processes employing the action of sulphur on one or more mercaptans in liquid state. When the mercaptan used contains more than 6 carbon atoms, it is reeoommended to perform the polysulphide synthesis at a temperature of the order of 60° to 150° C. and, in particular, between 70° and 140° C., which is proportionately lower the higher the sulphur rank desired in the case of the polysulphide. Thus, for example, using tert-dodecyl mercaptan, rank 5, namely $RS_5R$, can be obtained at 75° C. and rank 3, that is to say $RS_3R$, at 130° C.

The preferred relative pressures lie between 0.4 and 1 bar.

Since the reaction is:

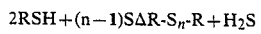

$2RSH+(n-1)S \Delta R-S_n-R+H_2S$ the molar ratio S/RSH required to produce a polysulphide of sulphur rank n is calculated as $(n-1):2$.

The process of the invention is particularly highly suitable for continuous operation, since it is possible for the three starting materials, mercaptan, sulphur and catalyst, to be introduced simultaneously in liquid state into a reactor. In this mode of operation, the crude product produced in a first reactor is subjected to a degassing operation, particularly by blowing nitrogen in, in a suitable apparatus, before being conveyed into a second reactor, where the reaction is completed.

After filtration, a polysulphide which should no longer contain any catalyst is collected.

In continuous production, the catalyst feed to the reactor may come from by a production of this catalyst which is also continuous. A plant for preparing the catalyst is then combined with the units for polysulphide production.

The invention is illustrated by the nonlimiting examples which follow.

EXAMPLE 1

Preparation of the novel catalyst 68 kg (0.3366 kmole) of tert-dodecyl mercaptan $C_{12}H_{25}SH$ and 6.3 kg of anhydrous NaOH (0.1575 kmole) are introduced into a 150-liter/reactor made of stainless steel. Good dispersion and homogenization of the mixture is ensured by heating for 5 hours at 80° C. Ethylene oxide is then injected into the reactor at a continuous rate of 7 kg/h; the relative pressure in the reactor rises from 0.2 bar at the beginning to 4 bars at the end of the reaction. The reaction mixture is next heated to 100°-110° C. for 2 hours and is then decompressed and degassed by passing nitrogen through, so as to remove all the excess ethylene oxide which has dissolved. The liquid obtained is subjected to a filtration which retains solid particles down to 5 m$\mu$. The resulting catalyst system has the composition:

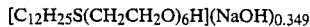

that is to say:

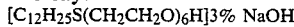

namely, on a weight basis:
$C_{12}H_{25}SH \ldots 42\%$
$CH_2CH_2O \ldots 55\%$
$NaOH \ldots 3\%$ The cloud point of this catalyst is approximately 62° C.

EXAMPLE 2

Production of di-tert-nonyl trisulphide $(C_9H_{19})_2S_3$.

Using two reactors in series, as described earlier, tert-nonyl mercaptan and molten sulphur are employed in a proportion of 1 atom of S per 1 mole of $C_9H_{19}SH$, i.e. 20 kg of S per 100 kg of mercaptan. 1.25 kg of catalyst $C_9H_{19}S(CH_2CH_2O)_6H \cdot (NaOH)_{0.349}$, prepared in a manner similar to that shown in Example 1, are added to 100 kg of mercaptan. The mixture is heated in the first reactor at 130° C. for 1 h 15 min and is subjected to degassing by blowing in 18 Nm$^3$ of nitrogen per 100 kg of starting mercaptan. The final heating then takes place in the second reactor, for 2 h 30 min at 130° C., and degassing is carried out using 18 Nm$^3$ of N$_2$ per 100 kg of mercaptan employed. When this production is carried out continuously, 800 kg of polysulphide can be obtained per hour, per m$^3$ of capacity of the main synthesis reactor.

EXAMPLE 3

Preparation of di-tert-dodecyl trisulphide $(C_{12}H_{25})_2S_3$.

The operating method is the same as in Example 2, but starting with tert-dodecyl mercaptan $C_{12}H_{25}SH$ to which 1.25% of catalyst obtained according to Example 1 has been added. The proportion of molten sulphur is 15.84 kg per 100 kg of mercaptan, all the remaining operating conditions being the same as in Example 2. The polysulphide is obtained in a yield of 98% based on the mercaptan employed, and the space time production rate is approximately 800 kg/h per m$^3$ of reactor, when operating continuously.

EXAMPLE 4

Production of di-tert-dodecyl pentasulphide $(C_{12}H_5)_2S_5$.

The operation is carried out, as above, with two reactors in series, but at the same temperature of 75° C. in both of these. The degassing operations also take place at 75° C., each with 18 Nm$^3$ of nitrogen per 100 kg of mercaptan. The quantity of sulphur employed is 2 atoms per mole of starting tert-dodecyl mercaptan, that is 31.9 kg of S per 100 kg of $C_{12}H_{25}SH$. The catalyst of Example 1 is added in a proportion of 0.4 kg per 100 kg of mercaptan. The relative pressure varies between 0.4 and 1 bar. When the process is carried out continuously, the space time production rate attains 1,000 kg of polysulphide per hour per m$^3$ of main synthesis reactor.

EXAMPLE 5

Continuous production of di-tert-dodecyl pentasulphide.

A first reactor, 150 l in capacity, is fed continuously with 80 kg per hour of tert-dodecyl mercaptan, 0.32 kg/h of catalyst according to Example 1 and with 22.8 kg/h of liquid sulphur. The reactor contents are maintained at 75° C. and are stirred vigorously by being circulated by a pump through a loop external to the reactor. The H$_2$S formed is removed to the flare, while the liquid leaving the reactor is subjected to degassing with nitrogen in a column provided for this purpose, using 5 Nm$^3$/h of nitrogen. This liquid travels into the second reactor, where it is again heated to 75° C. and then degassed with 10 Nm$^3$/h of nitrogen. After filtration at 60° C., 95 kg of finished product (98% yield) are obtained, with a residual SH content below 10 ppm, a sulphur content of 31.5% and a colour of $\leq$ 10 Gardner. This product exhibits no undesirable odour or turbidity.

EXAMPLE 6

Comparative

The operations of Example 4 are repeated, but with the oxyethylenated catalyst replaced by triethylamine. Even after the degassing, carried out as in Example 4, the polysulphide obtained has a disagreeable odour, marked colour and turbidity, whereas that of Example 4, according to the invention, no longer has any disagreeable odour and is clear. Furthermore, the strengthened basicity of the novel catalyst facilitates a faster and more complete conversion of the mercaptan.

EXAMPLE 7

Comparative

The operations of Example 3 are repeated, with the catalyst according to the invention being replaced by 0.125 mole of NaOH and 0.125 mole of hexanol per mole of tert-dodecyl mercaptan, as indicated in U.S. Pat. No. 3,340,324. The polysulphide is obtained in a yield of only 70% based on the mercaptan employed, instead of 98% in Example 3, and it is highly turbid, whereas that of Example 3 is perfectly homogeneous.

EXAMPLE 8

In Example 1, the catalyst according to the invention is replaced by the same quantity of corresponding sodium mercaptide. The reaction mixture is then heterogeneous and the product obtained is turbid.

These same disadvantages are found when the catalyst employed is sodium ethanolate.

Finally, the process according to the invention contributes the advantage of making it possible to produce polysulphide of a well determined mean sulphur rank, by virtue of the continuous feeding of the reactants, namely of sulphur and of the mercaptan, with appropriate stoichiometry. This is not achieved when operating noncontinuously, when the deficiency of sulphur, when it is fed in the mercaptan charge, results in the formation of polysulphides of lower ranks, which are undesirable. As already seen earlier, the invention causes the disappearance of the turbidity of the final products, which is due to the dissolved unreacted sulphur. The new process thus contributes better uniformity of manufacture and of the quality of the final products.

We claim:

1. A process for the production of organic polysulphides of the type $R-S_n-R$, where R is a hydrocarbon group and n a number from 2 to 8, by heating one or more mercaptans with sulphur, in the presence of a catalyst, said catalyst being obtained by condensing one molar equivalent of a mercaptan with 1 to 20 molar equivalents of an alkylene oxide in the presence of 0.01 to 1.5 molar equivalent of an alkaline base.

2. The process according to claim 1, wherein the catalyst corresponds to the formula : $R\text{-}S(C_mH_{2m}O)_xH \cdot (MOH)_y$ wherein R denotes a hydrocarbon group, m is a number from 2 to 4, x a number from 1 to 20, y is a number from 0.01 to 1, and M denotes an alkali metal.

3. The process according to claim 2, wherein x is 4 to 12, while y is 0.1 to 0.5.

4. The process according to claim 2, wherein R is a $C_1$–$C_{20}$ alkyl.

5. The process according to claim 2, wherein R is $C_6$–$C_{18}$ alkyl, and the alkylene oxide is ethylene oxide.

6. The process according to claim 5, wherein the alkyl is branched.

7. The process according to claim 6, wherein the alkyl is a tertiry alkyl.

8. The process according to claim 6, wherein the alkyl is tert-nonyl.

9. The process according to claim 6, wherein the alkyl is tert-dodecyl.

10. The process according to claim 1, wherein the heating takes place at a temperature from 60° to 150° C.

11. The process according to claim 1, wherein the heating takes place at a temperature of between 70° and 140° C.

12. The process according to claim 10, wherein n has a value of 3 to 5, said heating operation being carried out at a temperature which is proportionately higher the lower the desired number n.

13. The process according to claim 1, wherein the heating of the mercaptan with sulphur and the catalyst is carried out in two stages, each being followed by a degassing of $H_2S$.

14. The process according to claim 13, wherein said degassing of $H_2S$ is carried out by means of an inert gas.

15. The process according to claim 1, carried out at a relative pressure of 0.2 to 1 bar.

16. The process according to claim 1, wherein the catalyst is prepared by homogenizing one mole of mercaptan with $\alpha y$ moles ($\alpha = 1$ to 1.5) of alkaline base, preferably between 50° and 100° C., and then saturating the product obtained with alkylene oxide at a temperature of 80° to 120° C. at a relative pressure of 0.2 to 4 bars, followed by a degassing of the excess alkylene oxide.

17. The process according to claim 16, wherein said degassing of the excess alkylene oxide is carried out by means of an inert gas.

18. The process according to claim 16, wherein said mercaptan is $C_6$–$C_{18}$, said homogenization taking place between approximately 75° and 85° C. for 4 to 6 hours and the saturation with alkylene oxide at approximately 100° to 110° C.

19. The process according to claim 1, wherein the process is carried out continuously.

* * * * *